(12) United States Patent
Chae et al.

(10) Patent No.: US 11,964,932 B2
(45) Date of Patent: Apr. 23, 2024

(54) TRICYCLODECANE DIMETHANOL COMPOSITION AND PREPARATION METHOD OF THE SAME

(71) Applicant: SK CHEMICALS CO., LTD., Gyeonggi-do (KR)

(72) Inventors: Hee Il Chae, Gyeonggi-do (KR); Ju-Sik Kang, Gyeonggi-do (KR); Jeong Ho Park, Gyeonggi-do (KR); Song Lee, Gyeonggi-do (KR); Yu Mi Chang, Gyeonggi-do (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 0 days.

(21) Appl. No.: 18/003,432

(22) PCT Filed: May 20, 2022

(86) PCT No.: PCT/KR2022/007232
§ 371 (c)(1),
(2) Date: Dec. 27, 2022

(87) PCT Pub. No.: WO2022/265240
PCT Pub. Date: Dec. 22, 2022

(65) Prior Publication Data
US 2023/0192579 A1    Jun. 22, 2023

(30) Foreign Application Priority Data

Jun. 18, 2021  (KR) .................. 10-2021-0079300

(51) Int. Cl.
| | | |
|---|---|---|
| *C07C 29/141* | (2006.01) | |
| *B01J 31/22* | (2006.01) | |
| *C07C 31/27* | (2006.01) | |
| *C07C 45/50* | (2006.01) | |
| *C08G 63/199* | (2006.01) | |
| *B01J 21/18* | (2006.01) | |
| *B01J 23/46* | (2006.01) | |

(52) U.S. Cl.
CPC ......... *C07C 31/278* (2013.01); *B01J 31/2213* (2013.01); *C07C 29/141* (2013.01); *C07C 45/50* (2013.01); *C08G 63/199* (2013.01); *B01J 21/18* (2013.01); *B01J 23/462* (2013.01); *B01J 2531/82* (2013.01); *C07C 2603/68* (2017.05)

(58) Field of Classification Search
CPC . C07C 31/278; C07C 2603/68; C07C 29/141; C07C 45/50
See application file for complete search history.

(56) References Cited

U.S. PATENT DOCUMENTS

| | | | |
|---|---|---|---|
| 4,262,147 A | 4/1981 | Garrou et al. | |
| 6,365,782 B1 | 4/2002 | Nakamura et al. | |
| 6,794,482 B2 * | 9/2004 | Gloeckner | ............ C08L 101/00 524/556 |
| 7,144,975 B2 * | 12/2006 | Gloeckner | ........... C08G 63/553 524/556 |
| 10,538,472 B1 | 1/2020 | Chou et al. | |
| 10,767,004 B1 | 9/2020 | Chiu et al. | |
| 2005/0107644 A1 | 5/2005 | Lappe et al. | |
| 2005/0272960 A1 | 12/2005 | Dukat et al. | |
| 2008/0039593 A1 * | 2/2008 | Glockner | ................ C08L 67/06 525/450 |
| 2021/0253507 A1 | 8/2021 | Chae et al. | |

FOREIGN PATENT DOCUMENTS

| | | | | |
|---|---|---|---|---|
| JP | H11-080068 | | 3/1999 | |
| JP | H1180068 A | * | 3/1999 | ............. B01J 31/04 |
| JP | 2001-010999 | | 1/2001 | |
| KR | 10-2005-0044847 | | 5/2005 | |
| KR | 10-1200288 | | 11/2012 | |
| KR | 10-2019-0142208 | | 12/2019 | |
| KR | 10-2020-0136484 | | 12/2020 | |
| KR | 10-2389695 | | 4/2022 | |
| WO | WO 2020/164598 | | 8/2020 | |

OTHER PUBLICATIONS

Garlaschelli et al., "Hydroformylation and hydrocarbonylation of dicyclopentadiene with cobalt-rhodium catalytic systems promoted by triphenylphosphine: Synthesis of monoformyltricyclodecenes, diformyltricyclodecanes and di(tricyclodecenyl)ketones," Journal of Molecular Catalysis, vol. 68, 1991, abstract only.

Lange et al., "Three times faster to gel point," Adhesion Adhesives & Sealants, vol. 13, 2016, pp. 14-19.

International Search Report and Written Opinion for International (PCT) Patent Application No. PCT/KR2022/007232, dated Aug. 22, 2022, 8 pages.

* cited by examiner

*Primary Examiner* — Rosalynd A Keys
(74) *Attorney, Agent, or Firm* — Sheridan Ross P.C.

(57) ABSTRACT

Provided are a tricyclodecane dimethanol composition, in which a ratio of structural isomers is controlled, and a preparation method thereof.

7 Claims, 1 Drawing Sheet

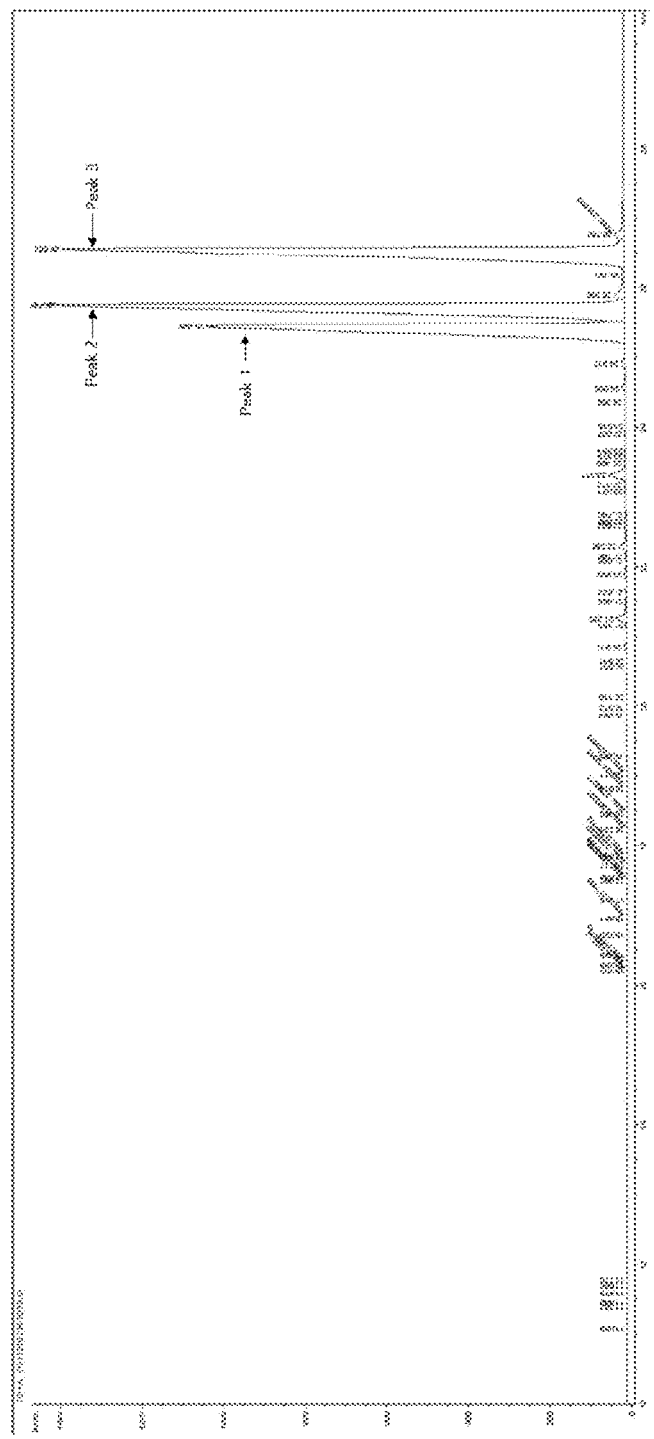

TRICYCLODECANE DIMETHANOL COMPOSITION AND PREPARATION METHOD OF THE SAME

TECHNICAL FIELD

Cross-Reference to Related Application

This application is a national stage application under 35 U.S.C. 371 and claims the benefit of PCT Application NO. PCT/KR2022/007232 having an international filing date of May 20, 2022, which designated the U.S., and which PCT application claimed the benefit of Korean Patent Application No. 10-2021-0079300, filed on Jun. 18, 2021, the contents of each of which are incorporated herein by reference in their entireties.

The present invention relates to a tricyclodecane dimethanol composition, in which a ratio of structural isomers is controlled, and a preparation method thereof.

Background Art

Tricyclodecane dimethanol (3(4), 8(9)-dihydroxymethyl-tricyclo[5.2.1.0$^{2,6}$]decane, TCDDM) is a material used as a monomer in the preparation of polymers such as polyester, polyacrylate, etc.

Tricyclodecane dimethanol may be prepared by performing hydroformylation of dicyclopentadiene (DCPD) to prepare tricyclodecane dialdehyde (TCDDA), followed by hydrogenation thereof, as disclosed in Korean Patent No. 10-1200288.

TCDDM prepared by such a method is a mixture of various structural isomers and stereoisomers, and a polyester resin prepared using the same is characterized in that its crystallization is difficult. Therefore, it is suitable for use as a coating agent for coating the inner surface of a can, etc. On the other hand, since resins for use in coating are required to exhibit good solubility in organic solvents in order to exhibit high processability, it is necessary to develop a TCDDM composition capable of improving the solubility of polyester resins.

PRIOR ART DOCUMENT

Patent Document 1: Korean Patent No. 10-1200288

DISCLOSURE

Technical Problem

There are provided a tricyclodecane dimethanol composition which may be suitably used in preparing a polyester having excellent solubility in organic solvents, wherein a ratio of structural isomers in the tricyclodecane dimethanol composition is controlled, and a preparation method thereof.

Technical Solution

To achieve the above objects, there is provided a tricyclodecane dimethanol composition including
20 parts by weight to 35 parts by weight of a first structural isomer represented by the following Formula 1-1,
27 parts by weight to 42 parts by weight of a second structural isomer represented by the following Formula 1-2, and
27 parts by weight to 42 parts by weight of a third structural isomer represented by the following Formula 1-3:

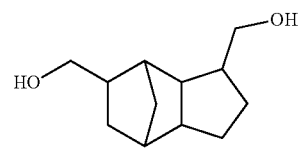

[Formula 1-1]

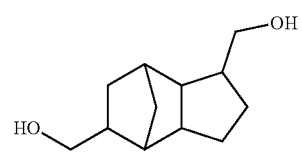

[Formula 1-2]

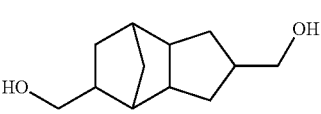

[Formula 1-3]

There is also provided a method of preparing the tricyclodecane dimethanol composition, the method including the steps of:
performing a hydroformylation reaction by adding dropwise dicyclopentadiene while maintaining a mixed gas of hydrogen and carbon monoxide at a pressure of 20 bar to 150 bar in the presence of a catalyst composition including a rhodium-containing catalyst compound and 5 moles to 200 moles of an organophosphorus compound per 1 mole of rhodium, and a dienophile; and
performing a hydrogenation reaction of tricyclodecane dialdehyde obtained by the hydroformylation reaction in the presence of a hydrogenation catalyst.

Effect of the Invention

A tricyclodecane dimethanol composition of the present invention may be suitably used in preparing a polyester having excellent solubility in organic solvents by controlling a ratio of structural isomers. In addition, according to a method of preparing the tricyclodecane dimethanol composition of the present invention, it is possible to prepare the tricyclodecane dimethanol composition, in which the ratio of structural isomers is controlled, with high efficiency and yield.

BRIEF DESCRIPTION OF DRAWINGS

FIG. 1 shows a gas chromatogram of a tricyclodecane dimethanol composition according to one exemplary embodiment of the present invention.

BEST MODE FOR CARRYING OUT THE INVENTION

Hereinafter, the present invention will be described in detail.

Tricyclodecane Dimethanol Composition

A tricyclodecane dimethanol composition of the present invention includes three types of TCDDM structural isomers represented by the following Formulae 1-1 to 1-3.

Specifically, the tricyclodecane dimethanol composition includes 20 parts by weight to 35 parts by weight of a first structural isomer represented by the following Formula 1-1, 27 parts by weight to 42 parts by weight of a second structural isomer represented by the following Formula 1-2, and 27 parts by weight to 42 parts by weight of a third structural isomer represented by the following Formula 1-3:

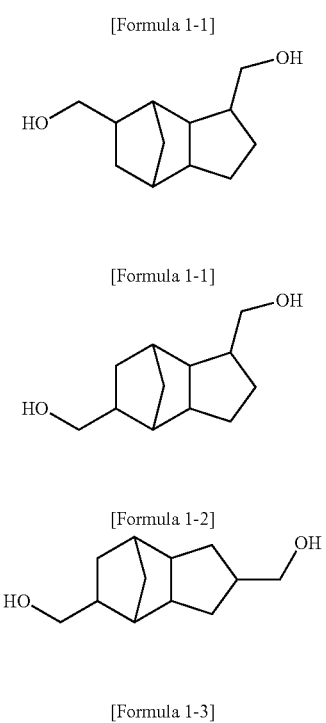

[Formula 1-1]

[Formula 1-1]

[Formula 1-2]

[Formula 1-3]

Tricyclodecane dimethanol (TCDDM) may be prepared by a preparation method including preparing tricyclodecane dialdehyde (DCDDA) by hydroformylation of dicyclopentadiene (DCPD), and then reducing DCDDA. Since the hydroformylation reaction of DCPD has low regioselectivity, a total of three types of TCDDA structural isomers are prepared at the same time. By performing a hydrogenation reaction of a mixture of these TCDDA structural isomers, a TCDDM composition including the three types of TCDDM structural isomers is prepared.

The present inventors have studied a tricyclodecane dimethanol composition suitable for use as a monomer in the preparation of a polyester for coating, and as a result, they found that when the tricyclodecane dimethanol composition including the three types of structural isomers in a predetermined ratio is used in the preparation of a polyester, solubility of the polyester may be further improved, thereby completing the present invention.

Accordingly, the tricyclodecane dimethanol composition according to one embodiment of the present invention satisfies the content of each isomer within the above range, thereby being usefully used in preparing a polyester having excellent solubility in organic solvents.

More preferably, the tricyclodecane dimethanol composition may include 22 parts by weight to 30 parts by weight of the first structural isomer, 30 parts by weight to 36 parts by weight of the second structural isomer, and 32 parts by weight to 40 parts by weight of the third structural isomer, based on 100 parts by weight of the composition.

The three types of TCDDM structural isomers are eluted at different retention times during gas chromatography (GC) analysis. Therefore, the contents of the first to third isomers in the TCDDM composition may be identified by analysis through gas chromatography.

Specifically, the gas chromatography analysis may be performed under the following conditions. 1 μl of the TCDDM composition is loaded onto a column having a length of 30 m, an inner diameter of 250 and a film thickness of 0.25 μm. An oven is heated from an initial temperature of 100° C. to 200° C. at a rate of 10° C./min, then heated to 250° C. again at a rate of 3° C./min, held at 250° C. for 30 minutes, and then gas chromatography analysis is performed using nitrogen as a carrier gas under conditions of an inlet temperature of 300° C., a detector temperature of 260° C., a flow rate of 1 mL/min, and a split ratio of 30:1.

Under these conditions, the first structural isomer is eluted at a retention time of 25.4 min to 25.5 min, the second structural isomer is eluted at a retention time of 25.7 min to 25.8 min, and the third structural isomer is eluted at a retention time of 26.5 min to 26.6 min (FIG. 1). In this regard, the relative content of each compound may be derived by comparing the area of each peak with respect to the total area of the elution peak (excluding the solvent peak) of the TCDDM composition.

The gas chromatography analysis conditions may be further specified in exemplary embodiments to be described later.

Based on 100 parts by weight of the tricyclodecane dimethanol composition, the contents of the three types of TCDDM structural isomers may be 89 parts by weight or more, 90 parts by weight or more, or 94 parts by weight or more, and 100 parts by weight or less. Meanwhile, the remainder of the composition, other than the three types of TCDDM structural isomers, may be tricyclodecane monomethanol, cyclopentadiene oligomer, C12 aliphatic diols derived from co-dimer components of cyclopentadiene and C4-C5 monomers (e.g., isoprene, piperylene, butadiene, etc.) in the cyclopentadiene raw materials, etc.

Method of Preparing Tricyclodecane Dimethanol Composition

The tricyclodecane dimethanol composition may be prepared by, for example, a preparation method including the following steps of:

i) performing a hydroformylation reaction by adding dropwise dicyclopentadiene while maintaining a mixed gas of hydrogen and carbon monoxide at a pressure of 20 bar to 150 bar in the presence of a catalyst composition including a rhodium-containing catalyst compound and 5 moles to 200 moles of an organophosphorus compound per 1 mole of rhodium, and a dienophile; and ii) performing a hydrogenation reaction of tricyclodecane dialdehyde obtained by the hydroformylation reaction in the presence of a hydrogenation catalyst.

Hereinafter, each step of the method of preparing the tricyclodecane dimethanol composition according to one embodiment of the present invention will be described.

i) Step of Performing Hydroformylation Reaction of Dicyclopentadiene

The step i) is a step of preparing tricyclodecane dialdehyde (TCDDA) by hydroformylation of dicyclopentadiene (DCPD). In this step, the structure of the tricyclodecane dimethanol (TCDDM) finally prepared is determined according to the position at which the formyl group is introduced. Accordingly, the content of the three types of TCDDM structural isomers in the tricyclodecane dimethanol composition finally prepared may be controlled by controlling the reaction conditions of the step i).

Specifically, in the present invention, the tricyclodecane dimethanol composition satisfying the above composition may be prepared by performing the hydroformylation reaction in the presence of dienophile, controlling the content of a ligand in the catalyst composition and a reaction pressure, and adding dropwise the raw material DCPD into a reactor including the catalyst composition.

The catalyst composition used in the hydroformylation reaction includes a rhodium-containing catalyst compound and an organophosphorus compound as a ligand.

The rhodium-containing catalyst compound applicable in the present invention is not particularly limited, as long as it forms a complex with the organophosphorus compound to exhibit hydroformylation activity in the presence of hydrogen and carbon monoxide. For example, one or more selected from the group consisting of $Rh(acac)(CO)_2$, $Rh_2O_3$, $Rh_4(CO)_{12}$, $Rh_6(CO)_{16}$, $Rh(NO_3)_3$, $Rh(CO_2(C1\sim C8))$, Rh/Al, and Rh/C may be used. Among them, $Rh(acac)(CO)_2$ may be preferably used.

In the known TCDDA preparation method, the rhodium compound is used in an amount of 70 ppm to 300 ppm in order to increase the conversion rate. However, when it is used at such a high concentration, a separate process is further required to recover the expensive rhodium catalyst, and thus there has been a problem in that the efficiency and economic feasibility of the TCDDA preparation process are reduced. In contrast, in the present invention, since hydroformylation is performed by adding dropwise DCPD in small amounts without adding at once, it is possible to obtain excellent TCDDA conversion rate even with a significantly reduced amount of catalyst. Thus, a separate process of recovering the catalyst is not required, thereby greatly improving the efficiency of the process.

In the present invention, the rhodium-containing catalyst compound is preferably used in the range of 1 ppm to 50 ppm, or 10 ppm to 35 ppm, or 10 ppm to 20 ppm (based on the rhodium element) of the total weight of the reactant dicyclopentadiene. When the content of the rhodium-containing catalyst compound is less than 1 ppm relative to the weight of dicyclopentadiene, the amount of the catalyst is too small and the hydroformylation reaction does not properly occur, and therefore, the conversion rate may decrease. When the rhodium-containing catalyst compound is used in excess of 50 ppm, there may be a problem in that impurities due to side reactions are generated, and a separate process of recovering the catalyst is required. Thus, the above-described effect may not be achieved. For this reason, it is preferable to satisfy the above range.

The rhodium-containing catalyst compound may exhibit catalytic activity by forming a complex with the organophosphorus compound in the organic solvent. In this regard, the applicable organophosphorus compound may be phosphine, phosphite, etc., and preferably, phosphite having a formula of $P(OR^1)(OR^2)(OR^3)$ (wherein $R^1$, $R^2$, and $R^3$ are each independently a substituted or unsubstituted alkyl group or aryl group). Specifically, the organophosphorus compound may be one or more selected from the group consisting of triphenylphosphite, tri s(2-t-butylphenyl)phosphite, tri s(3-methyl-6-t-butylphenyl)phosphite, tris(3-methoxy-6-t-butylphenyl)phosphite, tris(2,4-di-t-butylphenyl)phosphite, and di(2-t-butylphenyl)phosphite, but is not limited thereto.

The amount of the organophosphorus compound may be adjusted according to the content of rhodium in the catalyst composition. In one embodiment, the organophosphorus compound is used in an amount of 5 moles to 200 moles per 1 mole of rhodium. When the content of the organophosphorus compound satisfies the above range, the content of the ligand per catalyst is sufficient, and thus the hydroformylation reaction may proceed smoothly. Preferably, the organophosphorus compound may be used in an amount of 10 moles or more, 15 moles or more, or 25 moles or more, and 170 moles or less, 150 moles or less, 100 moles or less per 1 mole of rhodium.

In particular, in the present invention, the hydroformylation reaction is performed in the presence of a dienophile, and thus a high conversion rate may be obtained even with the content of the ligand lower than that before. Accordingly, according to the present invention, even with the content of the organophosphorus compound of 15 mole to 50 mole, or 15 mole to 25 mole per 1 mole of rhodium, an excellent TCDDA conversion rate of 90% or more or 94% or more may be obtained, and as a result, it is possible to further increase the TCDDM content in the final TCDDM composition.

The organic solvent applicable to the catalyst composition is not particularly limited, and commonly known inert organic solvents may be appropriately used. Specifically, the organic solvent may include aromatic hydrocarbon compounds, aliphatic hydrocarbon compounds, and alicyclic hydrocarbon compounds.

As the aromatic hydrocarbon compounds, methylbenzenes such as benzene, toluene, xylene, mesitylene, pseudocumene, etc., ethylbenzenes such as ethylbenzene, diethylbenzene, triethylbenzene, etc., propyl benzenes such as isopropylbenzene, 1,3-diisopropyl benzene, 1,4-diisopropyl benzene, etc., and other various alkyl benzenes may also be suitably used. As the aliphatic hydrocarbon compounds, pentane, hexane, heptane, octane, isooctane, dodecane, and decane may be exemplified, but they are not limited thereto, as long as they are a liquid at standard temperature and pressure. As the alicyclic hydrocarbon compounds, cyclohexane, cyclooctane, cyclododecane, decalin, methyl cyclohexane, etc. may be suitably used.

The concentration of the catalyst composition is not particularly limited, but it may be, for example, in the range of 0.01 mM to 5.0 mM, or 0.05 mM to 0.5 mM, based on the rhodium element. When the concentration of the catalyst composition is less than the above range, there may be a problem in that the catalyst reactivity deteriorates due to the excessively low concentration of the catalyst, and when the concentration exceeds the above range, there may be a problem in that the cost of the process increases due to excessive use of the catalyst. Accordingly, the concentration is properly controlled within the above range.

The hydroformylation reaction of DCPD is performed under a mixed gas atmosphere of hydrogen and carbon monoxide, wherein the pressure of the mixed gas is preferably maintained at 20 bar to 150 bar. When the reaction pressure is less than 20 bar, the hydroformylation reaction may not proceed smoothly, and when it exceeds 150 bar, a side reaction may occur to lower the TCDDA yield. More preferably, the pressure of the mixed gas may be 20 bar or more, 30 bar or more, or 50 bar or more, and 120 bar or less, or 100 bar or less.

In this regard, for smooth progress of the hydroformylation reaction, a volume ratio of hydrogen and carbon monoxide is preferably in the range of 1:10 to 10:1, more preferably, in the range of 1:2 to 2:1.

Under the pressure conditions as described above, the temperature of the hydroformylation reaction step is preferably 50° C. to 100° C., more preferably, 70° C. to 90° C., or 75° C. to 85° C. When the reaction temperature is lower than 50° C., smooth progress of the reaction may be difficult and the yield may decrease. When the reaction temperature is too high by exceeding 100° C., the retro Diels-Alder reaction of DCPD and Cp oligomerization by the Diels-Alder reaction of cyclopentadiene (Cp) generated by the retro Diels-Alder reaction and DCPD may occur.

Meanwhile, in the hydroformylation reaction step of the present invention, the raw material DCPD is added in a dropwise manner to the reactor including the catalyst composition, thereby achieving the excellent conversion rate even with a small amount of the catalyst and minimizing side reactions.

When DCPD is added in a dropwise manner, the concentration of DCPD relative to the concentration of the catalyst composition in the reactor is maintained low, and thus Cp oligomerization that may occur in the presence of a high concentration of DCPD may be suppressed. In addition, since the concentration of DCPD in the reactor may be controlled by controlling the dropwise addition rate, a high conversion rate may be achieved even with relatively small amounts of the catalyst compound and the ligand.

DCPD introduced into the reactor may be prepared in the form of a solution. In this regard, as the organic solvent, an organic solvent applicable to the catalyst composition may be used. The organic solvent used for the catalyst composition and the organic solvent used for the DCPD solution are not necessarily the same as each other, but it is preferable that the same solvent is used, because the reaction may smoothly proceed.

The DCPD concentration in the DCPD solution is not particularly limited, and for example, it may be in the range of 0.1 M or more, or 1.0 M to 7.6 M. When the concentration of the DCPD solution is less than the above range, the concentration of the rhodium-containing catalyst compound and the organophosphorus compound in the reactor decreases, as the dropwise addition proceeds, and thus there may be a problem in that the hydroformylation reaction does not proceed smoothly. Accordingly, the concentration is appropriately controlled within the above range.

The dropwise addition rate of DCPD may be controlled according to the concentration of the dicyclopentadiene solution and the capacity of the catalyst composition, and the number of moles of dicyclopentadiene added per minute with respect to 1 mmol of the catalyst (based on the rhodium element) of the catalyst composition is preferably allowed to be 10 mmol to 10,000 mmol, or 100 mmol to 1,000 mmol, or 100 mmol to 500 mmol.

When the dropwise addition rate is too fast by exceeding the above range, it is difficult to achieve the above-mentioned effect due to by-product generation, and when the dropwise addition rate is too slow, the overall reaction rate may become slow, and the process efficiency may be reduced. Accordingly, it is preferable to satisfy the above range.

Meanwhile, the hydroformylation reaction step of DCPD is performed in the presence of a dienophile. Examples of the dienophile may include one or more selected from the group consisting of maleic anhydride, tetracyanoethylene, maleic acid, maleonitrile, 2-methylenemalononitrile, dialkyl 2-methylenemalonate (the number of carbon atoms in the alkyl group is each independently 1 to 10), 2-methylenemalonic acid, 2-methylenemalonaldehyde, 3-methylenepentane-2,4-dione, fumaraldehyde, ethene-1,1,2,2-tetracarbaldehyde, 1,4-benzoquinone, and dialkyl maleate (the number of carbon atoms in the alkyl group is each independently 1 to 10). Preferably, as the dienophile, one or more selected from the group consisting of maleic anhydride, maleic acid, maleonitrile, and 1,4-benzoquinone may be used.

DCPD is usually prepared through dimerization of cyclopentadiene which is obtained in a naphtha cracking process. In this process, C4 to C5 diene compounds, for example, compounds such as isoprene, piperylene, butadiene, etc., may exist as a trace amount of impurities in DCPD. However, when the diene compounds are bound with the rhodium-containing catalyst used in the hydroformylation reaction, the binding time is very long, and as a result, there is a problem in that the rhodium-containing catalyst is deactivated.

Therefore, the dienophile capable of removing the diene contained in the DCPD raw materials may be used as an additive to prevent the deactivation of the rhodium-containing catalyst, thereby further improving the hydroformylation reaction rate. The dienophile causes the Diels-Alder reaction with the diene under the above-described hydroformylation reaction conditions, thereby preventing the diene from binding with the rhodium-containing catalyst.

To achieve the above effect, the dienophile may be included in an amount of 0.001 part by weight to 1.0 part by weight with respect to 100 parts by weight of dicyclopentadiene. Usually, the content of the diene compound is 0.0001 part by weight to 0.5 parts by weight, based on 100 parts by weight of the DCPD raw material. Thus, when the dienophile is added in the above range, it is sufficient to remove a trace amount of the diene compound. However, it is preferable not to exceed the above range because there is a risk that a side reaction may occur when an excessively large amount of dienophile is added. More preferably, the dienophile may be included in an amount of 0.005 to 0.5 parts by weight, or 0.01 to 0.1 part by weight, based on 100 parts by weight of dicyclopentadiene.

The dienophile may be mixed together with the DCPD solution or may be mixed together with the catalyst composition, and then fed into the reactor. Preferably, the dienophile is first mixed with the DCPD solution, and then the mixture is added dropwise to the reactor in which the catalyst composition is present, followed by the hydroformylation reaction.

The reaction mixture including TCDDA which is obtained after the hydroformylation reaction undergoes a purification process such as vacuum distillation, etc., or only a thin film evaporation process to remove the solvent without a separate purification step, and then injected for the hydrogenation reaction. For example, the reaction mixture may be subjected to the thin film evaporation under a pressure of 0.1 torr to 10 torr, or 0.1 torr to 1 torr and a temperature of 90° C. to 150° C., or 100° C. to 120° C. to remove the solvent, followed by the hydrogenation reaction.

ii) Step of Performing Hydrogenation Reaction of Tricyclodecane Dialdehyde

Next, the tricyclodecane dialdehyde (TCDDA) mixture prepared through the hydroformylation reaction of the step i) is hydrogenated in the presence of a catalyst to prepare a tricyclodecane dimethanol (TCDDM) mixture.

The hydrogenation reaction may be performed in a solution. As the reaction solvent, a lower alcohol such as methanol, ethanol, isopropanol, etc., water, or a combination thereof may be used. For example, a mixed solvent of water and isopropanol may be used.

As the hydrogenation catalyst, a metal catalyst generally used for hydrogenation of a carbonyl group, for example, a metal catalyst, such as nickel, platinum, palladium, rhodium, ruthenium, copper, chromium, etc., may be used. The metal catalyst may be used in an elemental form, an oxide form, a form of being supported on an inorganic carrier, or a metal complex form. For example, as the hydrogenation catalyst, a ruthenium catalyst (Ru/C) supported on a carbon support may be used.

The amount of the catalyst used may be appropriately adjusted in consideration of the efficiency of the hydrogenation reaction. For example, the hydrogenation catalyst may be used in an amount of 50 ppm to 5000 ppm, or 100 ppm to 500 ppm (based on the metal element) with respect to the total weight of the reactant tricyclodecane dialdehyde mixture. When the content of the catalyst is less than 50 ppm, the reaction rate may be too slow, and when the content exceeds 5000 ppm, the preparation cost increases due to excessive use of the catalyst without any particular advantage, and thus it is preferable to satisfy the above range.

The hydrogenation reaction may be performed at a temperature of 80° C. to 250° C. and a pressure of 20 bar to 200 bar, preferably at a temperature of 90° C. to 130° C. and a pressure of 60 bar to 80 bar. When the reaction temperature is lower than 80° C., or the reaction pressure (the pressure of the hydrogen gas) is less than 50 bar, the reaction rate may not be sufficient. When the reaction temperature is higher than 250° C., or the reaction pressure is higher than 200 bar, deactivation of the catalyst may be accelerated, and process costs may increase.

After the hydrogenation reaction, a purification step may be performed, as needed. For example, the reaction mixture may be filtered and subjected to vacuum fractional distillation to obtain the tricyclodecane dimethanol composition. The fractional distillation may be performed, for example, under conditions of a pressure of 0.1 torr to 10 torr, or 0.1 torr to 1 torr and a temperature of 100° C. to 250° C., or 150° C. to 220° C.

The tricyclodecane dimethanol composition prepared by the above-described preparation method may include 20 parts by weight to 35 parts by weight of the first structural isomer, 27 parts by weight to 42 parts by weight of the second structural isomer, and 27 parts by weight to 42 parts by weight of the third structural isomer, thereby being suitably used in preparing a polyester with excellent solubility in organic solvents.

Hereinafter, the actions and effects of the present invention will be described in more detail with reference to the specific exemplary examples of the present invention. However, these exemplary examples are provided only for illustrating the present invention, and the scope of the present invention is not defined thereby.

Comparative Example 1

(Step 1)
In a 1 L high-pressure reactor, 7.9 mg of $Rh(CO)_2(acac)$ (15 ppm, based on Rh, relative to dicyclopentadiene), and 100 mg of tris(2,4-di-tert-butylphenyl)phosphite were dissolved in 100 g of toluene, and then 210 g of dicyclopentadiene (DCPD) was added at once without dropwise addition, followed by mixing. The reaction mixture was heated to 85° C. and allowed to react for 3 hours while maintaining a pressure of a mixed gas ($CO:H_2$=1:1) at 100 bar.

(Step 2)
The reaction mixture in the step 1 without additional purification was further reacted for 3 hours while heating the mixture to 130° C. and maintaining the pressure of the $CO/H_2$ mixed gas at 100 bar. Then, a sample of the reaction mixture was taken and analyzed by gas chromatography. A conversion rate to TCDDA was 81%.

(Step 3)
The reaction mixture of the step 2 was concentrated under reduced pressure to remove toluene. The toluene-removed mixture was subjected to thin film evaporation under conditions of 0.2 torr and 130° C. to obtain 238.1 g (yield: 78.0%) of TCDDA (TCD-dialdehyde).

(Step 4)
200 g of TCDDA of the step 3, 100 g of isopropyl alcohol (IPA), 25 g of water, and 3 g of 5% Ru/C (wetted with ca. 50% Water) were mixed and put into a 600 ml high-pressure reactor. The mixture was allowed to react for 4 hours while heating to 130° C. and maintaining a pressure of $H_2$ gas at 70 bar. Then, a sample of the reaction mixture was taken and analyzed by gas chromatography.

(Step 5)
The reaction mixture of the step 4 was filtered to remove Ru/C, and subjected to vacuum distillation under conditions of 100° C./10 torr to remove isopropyl alcohol and water. The TCDDM (TCD-dimethanol) mixture thus obtained was subjected to vacuum fractional distillation under conditions of 150° C. to 220° C. and 0.1 torr to obtain 181 g of a final TCDDM composition.

Comparative Example 2

(Step 1)
In a 1 L high-pressure reactor, 7.9 mg of $Rh(CO)_2(acac)$ (15 ppm, based on Rh, relative to dicyclopentadiene), and 2 g of tris(2,4-di-tert-butylphenyl)phosphite were dissolved in 100 g of toluene, and then 210 g of dicyclopentadiene (DCPD) was added at once without dropwise addition, followed by mixing. The reaction mixture was heated to 85° C. and allowed to react for 3 hours while maintaining a pressure of a mixed gas ($CO:H_2$=1:1) at 100 bar.

(Step 2)
The reaction mixture in the step 1 without additional purification was further reacted for 3 hours while heating the mixture to 130° C. and maintaining the pressure of the $CO/H_2$ mixed gas at 100 bar. Then, a sample of the reaction mixture was taken and analyzed by gas chromatography. A conversion rate to TCDDA was 82%.

(Step 3)
The reaction mixture of the step 2 was concentrated under reduced pressure to remove toluene. The toluene-removed mixture was subjected to thin film evaporation under conditions of 0.2 torr and 130° C. to obtain 241.5 g (yield: 79.1%) of TCDDA (TCD-dialdehyde).

(Step 4)
200 g of TCDDA of the step 3, 100 g of isopropyl alcohol (IPA), 25 g of water, and 3 g of 5% Ru/C (wetted with ca. 50% Water) were mixed and put into a 600 ml high-pressure reactor. The mixture was allowed to react for 4 hours while heating to 130° C. and maintaining a pressure of $H_2$ gas at 70 bar. Then, a sample of the reaction mixture was taken and analyzed by gas chromatography.

(Step 5)
The reaction mixture of the step 4 was filtered to remove Ru/C, and subjected to vacuum distillation under conditions of 100° C./10 torr to remove isopropyl alcohol and water. The TCDDM (TCD-dimethanol) mixture thus obtained was subjected to vacuum fractional distillation under conditions of 150° C. to 220° C. and 0.1 torr to obtain 177 g of a final TCDDM composition.

Comparative Example 3

(Step 1)
In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 100 bar. A DCPD solution, in which 10 g of toluene and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

(Step 2)

The reaction mixture in the step 1 without additional purification was further reacted for 3 hours while heating the mixture to 130° C. and maintaining the pressure of the $CO/H_2$ mixed gas at 100 bar. Then, a sample of the reaction mixture was taken and analyzed by gas chromatography. A conversion rate to TCDDA was 94%.

(Step 3)

The reaction mixture of the step 2 was concentrated under reduced pressure to remove toluene. The toluene-removed mixture was subjected to thin film evaporation under conditions of 0.2 torr and 130° C. to obtain 278.4 g (yield: 91.1%) of TCDDA (TCD-dialdehyde).

(Step 4)

200 g of TCDDA of the step 3, 100 g of isopropyl alcohol (IPA), 25 g of water, and 3 g of 5% Ru/C (wetted with ca. 50% Water) were mixed and put into a 600 ml high-pressure reactor. The mixture was allowed to react for 4 hours while heating to 130° C. and maintaining a pressure of $H_2$ gas at 70 bar. Then, a sample of the reaction mixture was taken and analyzed by gas chromatography.

(Step 5)

The reaction mixture of the step 4 was filtered to remove Ru/C, and subjected to vacuum distillation under conditions of 100° C./10 torr to remove isopropyl alcohol and water. The TCDDM (TCD-dimethanol) mixture thus obtained was subjected to vacuum fractional distillation under conditions of 150° C. to 220° C. and 0.1 torr to obtain 179 g of a final TCDDM composition.

Comparative Example 4

In a 1 L high-pressure reactor, 7.9 mg of $Rh(CO)_2(acac)$ (15 ppm, based on Rh, relative to dicyclopentadiene), and 0.30 g of tris(2,4-di-tert-butylphenyl)phosphite were dissolved in 100 g of toluene, and then the mixture was heated to 75° C. while maintaining a pressure of a mixed gas ($CO:H_2$=1:1) at 100 bar. A DCPD solution, in which 10 g of toluene and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 75° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 78%. In the step 3, the result of thin film evaporation showed that TCDDA was obtained with a yield of 73.5%. After performing the procedure of the step 5, 180 g of a final TCDDM composition was obtained.

Comparative Example 5

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 20 bar. A DCPD solution, in which 10 g of toluene and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 20 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 20 bar. After the step 2, the result of GC analysis showed that a conversion rate to TCDDA was 72%. In the step 3, the result of thin film evaporation showed that TCDDA was obtained with a yield of 69%. After performing the procedure of the step 5, 178 g of a final TCDDM composition was obtained.

Comparative Example 6

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 70 bar. A DCPD solution, in which 10 g of toluene and 210 g of dicyclopentadiene (DCPD) were mixed, was slowly added dropwise to the high-pressure reactor for 3 hours at a rate of 2.6 ml/min (i.e., the amount of DCPD added dropwise per minute with respect to 1 mmol of Rh was 640 mmol). During dropwise addition of the DCPD solution, the temperature and the pressure inside the high-pressure reactor were maintained at 85° C. and 70 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 70 bar. After the step 2, the result of GC analysis showed that a conversion rate to TCDDA was 83%. In the step 3, the result of thin film evaporation showed that TCDDA was obtained with a yield of 87%. After performing the procedure of the step 5, 176 g of a final TCDDM composition was obtained.

Example 1

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 100 bar. A DCPD solution, in which 10 g of toluene, 100 mg of maleic anhydride (MA), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

(Step 2)

The reaction mixture in the step 1 without additional purification was further reacted for 3 hours while heating the mixture to 130° C. and maintaining the pressure of the $CO/H_2$ mixed gas at 100 bar. Then, a sample of the reaction mixture was taken and analyzed by gas chromatography. A conversion rate to TCDDA was 96%.

(Step 3)

The reaction mixture of the step 2 was concentrated under reduced pressure to remove toluene. The toluene-removed mixture was subjected to thin film evaporation under conditions of 0.2 torr and 130° C. to obtain 281.1 g (yield: 92.0%) of TCDDA (TCD-dialdehyde).

(Step 4)

200 g of TCDDA of the step 3, 100 g of isopropyl alcohol (IPA), 25 g of water, and 3 g of 5% Ru/C (wetted with ca. 50% Water) were mixed and put into a 600 ml high-pressure reactor. The mixture was allowed to react for 4 hours while heating to 130° C. and maintaining a pressure of $H_2$ gas at 70 bar. Then, a sample of the reaction mixture was taken and analyzed by gas chromatography.

(Step 5)

The reaction mixture of the step 4 was filtered to remove Ru/C, and subjected to vacuum distillation under conditions of 100° C./10 torr to remove isopropyl alcohol and water. The TCDDM (TCD-dimethanol) mixture thus obtained was subjected to vacuum fractional distillation under conditions of 150° C. to 220° C. and 0.1 torr to obtain 181 g of a final TCDDM composition.

Example 2

(Step 1)

In a 1 L high-pressure reactor, 7.9 mg of $Rh(CO)_2(acac)$ (15 ppm, based on Rh, relative to dicyclopentadiene), and 0.99 g of tris(2,4-di-tert-butylphenyl)phosphite were dissolved in 100 g of toluene, and then the mixture was heated to 85° C. while maintaining a pressure of a mixed gas ($CO:H_2=1:1$) at 100 bar. A DCPD solution, in which 10 g of toluene, 100 mg of maleic anhydride (MA), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 96%. In the step 3, the result of thin film evaporation showed that TCDDA was obtained with a yield of 92%. After performing the procedure of the step 5, 179 g of a final TCDDM composition was obtained.

Example 3

(Step 1)

In a 1 L high-pressure reactor, 7.9 mg of $Rh(CO)_2(acac)$ (15 ppm, based on Rh, relative to dicyclopentadiene), and 0.50 g of tris(2,4-di-tert-butylphenyl)phosphite were dissolved in 100 g of toluene, and then the mixture was heated to 85° C. while maintaining a pressure of a mixed gas ($CO:H_2=1:1$) at 100 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 95%. In the step 3, the result of thin film evaporation showed that TCDDA was obtained with a yield of 92%. After performing the procedure of the step 5, 180 g of a final TCDDM composition was obtained.

Example 4

(Step 1)

In a 1 L high-pressure reactor, 7.9 mg of $Rh(CO)_2(acac)$ (15 ppm, based on Rh, relative to dicyclopentadiene), and 0.50 g of tris(2,4-di-tert-butylphenyl)phosphite were dissolved in 100 g of toluene, and then the mixture was heated to 75° C. while maintaining a pressure of a mixed gas ($CO:H_2=1:1$) at 100 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 75° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 96%. In the step 3, the result of thin film evaporation showed that TCDDA was obtained with a yield of 94%. After performing the procedure of the step 5, 180 g of a final TCDDM composition was obtained.

Example 5

In a 1 L high-pressure reactor, 7.9 mg of $Rh(CO)_2(acac)$ (15 ppm, based on Rh, relative to dicyclopentadiene), and 0.30 g of tris(2,4-di-tert-butylphenyl)phosphite were dissolved in 100 g of toluene, and then the mixture was heated to 75° C. while maintaining a pressure of a mixed gas ($CO:H_2=1:1$) at 100 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 75° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 94%. In the step 3, the result of thin film evaporation showed that TCDDA was obtained with a yield of 91%. After performing the procedure of the step 5, 178 g of a final TCDDM composition was obtained.

Example 6

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 70 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 70 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 70 bar. After the step 2, the result of GC analysis showed that a conversion rate to TCDDA was 96%. In the step 3, the result of thin film evaporation showed that TCDDA was obtained with a yield of 93%. After performing the procedure of the step 5, 180 g of a final TCDDM composition was obtained.

Example 7

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 50 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 50 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 50 bar. After the step 2, the result of GC analysis showed that a conversion rate to TCDDA was 95%. In the step 3, the result of thin film evaporation showed that TCDDA was obtained with a yield of 91%. After performing the procedure of the step 5, 180 g of a final TCDDM composition was obtained.

Example 8

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 30 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 30 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 30 bar. After the step 2, the result of GC analysis showed that a conversion rate to TCDDA was 95%. In the step 3, the result of thin film evaporation showed that TCDDA was obtained with a yield of 92%. After performing the procedure of the step 5, 176 g of a final TCDDM composition was obtained.

Example 9

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2$=1:1) at 20 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 20 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 20 bar. After the step 2, the result of GC analysis showed that a conversion rate to TCDDA was 86%. In the step 3, the result of thin film evaporation showed that TCDDA was obtained with a yield of 84%. After performing the procedure of the step 5, 179 g of a final TCDDM composition was obtained.

Example 10

(Step 1)

In a 1 L high-pressure reactor, 7.9 mg of Rh(CO)$_2$(acac) (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas (CO:H$_2$=1:1) at 70 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 0.65 ml/min (i.e., the amount of DCPD added dropwise per minute with respect to 1 mmol of Rh was 160 mmol). During dropwise addition of the DCPD solution, the temperature and the pressure inside the high-pressure reactor were maintained at 85° C. and 70 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 70 bar. After the step 2, the result of GC analysis showed that a conversion rate to TCDDA was 96%. In the step 3, the result of thin film evaporation showed that TCDDA was obtained with a yield of 92%. After performing the procedure of the step 5, 182 g of a final TCDDM composition was obtained.

Example 11

(Step 1)

In a 1 L high-pressure reactor, 7.9 mg of Rh(CO)$_2$(acac) (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas (CO:H$_2$=1:1) at 70 bar. A DCPD solution, in which 10 g of toluene, 100 mg of maleic anhydride, and 210 g of dicyclopentadiene (DCPD) were mixed, was slowly added dropwise to the high-pressure reactor for 3 hours at a rate of 2.6 ml/min (i.e., the amount of DCPD added dropwise per minute with respect to 1 mmol of Rh was 640 mmol). During dropwise addition of the DCPD solution, the temperature and the pressure inside the high-pressure reactor were maintained at 85° C. and 70 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 70 bar. After the step 2, the result of GC analysis showed that a conversion rate to TCDDA was 96%. In the step 3, the result of thin film evaporation showed that TCDDA was obtained with a yield of 92%. After performing the procedure of the step 5, 182 g of a final TCDDM composition was obtained.

Example 12

(Step 1)

In a 1 L high-pressure reactor, 7.9 mg of Rh(CO)$_2$(acac) (15 ppm, based on Rh, relative to dicyclopentadiene), and 0.30 g of tris(2,4-di-tert-butylphenyl)phosphite were dissolved in 100 g of toluene, and then the mixture was heated to 75° C. while maintaining a pressure of a mixed gas (CO:H$_2$=1:1) at 100 bar. A DCPD solution, in which 10 g of toluene, 100 mg of 1,4-benzoquinone (1,4-BQ), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 75° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 95%. In the step 3, the result of thin film evaporation showed that TCDDA was obtained with a yield of 93%. After performing the procedure of the step 5, 178 g of a final TCDDM composition was obtained.

Example 13

(Step 1)

In a 1 L high-pressure reactor, 7.9 mg of Rh(CO)$_2$(acac) (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas (CO:H$_2$=1:1) at 30 bar. A DCPD solution, in which 10 g of toluene, 100 mg of 1,4-benzoquinone (1,4-BQ), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 30 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 20 bar. After the step 2, the result of GC analysis showed that a conversion rate to TCDDA was 95%. In the step 3, the result of thin film evaporation showed that TCDDA was obtained with a yield of 94%. After performing the procedure of the step 5, 179 g of a final TCDDM composition was obtained.

Example 14

(Step 1)

In a 1 L high-pressure reactor, 7.9 mg of Rh(CO)$_2$(acac) (15 ppm, based on Rh, relative to dicyclopentadiene), and 0.30 g of tris(2,4-di-tert-butylphenyl)phosphite were dissolved in 100 g of toluene, and then the mixture was heated to 75° C. while maintaining a pressure of a mixed gas (CO:H$_2$=1:1) at 100 bar. A DCPD solution, in which 10 g of toluene, 100 mg of maleic acid (MAD), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 75° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 94%. In the step 3, the result of thin film evaporation showed that TCDDA was obtained with a yield of 91%. After performing the procedure of the step 5, 178 g of a final TCDDM composition was obtained.

Example 15

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2=1:1$) at 30 bar. A DCPD solution, in which 10 g of toluene, 100 mg of maleic acid (MAD), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 30 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 20 bar. After the step 2, the result of GC analysis showed that a conversion rate to TCDDA was 96%. In the step 3, the result of thin film evaporation showed that TCDDA was obtained with a yield of 93%. After performing the procedure of the step 5, 179 g of a final TCDDM composition was obtained.

Example 16

(Step 1)

In a 1 L high-pressure reactor, 7.9 mg of $Rh(CO)_2(acac)$ (15 ppm, based on Rh, relative to dicyclopentadiene), and 0.30 g of tris(2,4-di-tert-butylphenyl)phosphite were dissolved in 100 g of toluene, and then the mixture was heated to 75° C. while maintaining a pressure of a mixed gas ($CO:H_2=1:1$) at 100 bar. A DCPD solution, in which 10 g of toluene, 100 mg of maleonitrile (MN), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 75° C. and 100 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the result of GC analysis showed that a conversion rate to TCDDA was 94%. In the step 3, the result of thin film evaporation showed that TCDDA was obtained with a yield of 92%. After performing the procedure of the step 5, 178 g of a final TCDDM composition was obtained.

Example 17

(Step 1)

In a 1 L high-pressure reactor, 7.9 mg of $Rh(CO)_2(acac)$ (15 ppm, based on Rh, relative to dicyclopentadiene), and 1.98 g of tris(2,4-di-tert-butylphenyl)phosphite were dissolved in 100 g of toluene, and then the mixture was heated to 85° C. while maintaining a pressure of a mixed gas ($CO:H_2=1:1$) at 30 bar. A DCPD solution, in which 10 g of toluene, 100 mg of maleonitrile (MN), and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 30 bar, respectively. After completing the dropwise addition of the DCPD solution, the reaction was further allowed under the same temperature and pressure conditions for 1.5 hours.

Thereafter, the procedures of steps 2 to 5 were performed in the same manner as in Example 1. In the step 2, the reaction was allowed while maintaining the pressure at 20 bar. After the step 2, the result of GC analysis showed that a conversion rate to TCDDA was 95%. In the step 3, the result of thin film evaporation showed that TCDDA was obtained with a yield of 93%. After performing the procedure of the step 5, 179 g of a final TCDDM composition was obtained.

[Gas Chromatography (GC) Analysis]

The isomer content of each of the TCDDM compositions obtained in Examples and Comparative Examples was analyzed by gas chromatography.

Agilent 7890B (GC-FID) as an instrument and DB-WAX (length of 30 m×inner diameter of 250 μm×film thickness of 0.25 μm) model as a column were used, and an oven was heated at a rate of 10° C./min from an initial temperature of 100° C. to 200° C. The temperature was again raised to 250° C. at a rate of 3° C./min, and maintained at 250° C. for 30 minutes, followed by analysis. An inlet temperature was 300° C., a detector temperature was 260° C., a flow rate was 1 mL/min, a split ratio was 30:1, a sample injection volume was 1 μl, and a carrier gas was nitrogen.

Detailed analysis conditions are as follows.

<Inlet>

Heater: 300° C., Pressure: 13.599 psi, Total Flow: 33 ml/min, Septum Purge Flow: 2 ml/min Split Ratio: 30:1

<Column>

DB-WAX, 30 m×250 μm×0.25 Agilent

Mode: constant flow, Nominal initial flow: 1.0 mL/min, Average velocity: 28.23 cm/sec <Detector (Fid)>

Temperature: 260° C. (On), Hydrogen flow: 35.0 mL/min (On), Air flow: 350.0 mL/min (On), Makeup flow: 25.0 mL/min (On)

Makeup Gas Type: Nitrogen

TABLE 1

| | Dienophile | Reaction temperature of Step 1 (° C.) | Reaction pressure of Step 1 (bar) | Equivalent of ligand (eq)[1] | Dropwise addition rate of raw material[2] | TCDDM isomer composition (first/second/third structural isomers, %)[3] | TCDDA conversion rate (%)[4] | TCDDM content in TCDDM composition |
|---|---|---|---|---|---|---|---|---|
| Comparative Example 1 | — | 85 | 100 | 5 | — | 18.9/44.3/25.3 | 81 | 88.5 |
| Comparative Example 2 | — | 85 | 100 | 100 | — | 19.1/44.7/26.3 | 82 | 90.1 |
| Comparative Example 3 | — | 85 | 100 | 100 | 320 | 19.3/26.7/45.2 | 94 | 91.2 |
| Comparative Example 4 | — | 75 | 100 | 15 | 320 | 19.4/26.4/45.0 | 78 | 90.8 |
| Comparative Example 5 | — | 85 | 20 | 100 | 320 | 19.7/26.1/43.1 | 72 | 88.9 |
| Comparative Example 6 | — | 85 | 70 | 100 | 640 | 19.4/26.5/43.2 | 83 | 89.1 |
| Example 1 | MA | 85 | 100 | 100 | 320 | 25.3/31.6/39.9 | 96 | 96.8 |
| Example 2 | MA | 85 | 100 | 50 | 320 | 26.3/33.9/36.2 | 96 | 96.4 |
| Example 3 | MA | 85 | 100 | 25 | 320 | 25.6/35.3/33.6 | 95 | 94.5 |
| Example 4 | MA | 75 | 100 | 25 | 320 | 27.2/34.5/34.9 | 96 | 96.6 |
| Example 5 | MA | 75 | 100 | 15 | 320 | 23.4/37.6/35.7 | 94 | 96.7 |
| Example 6 | MA | 85 | 70 | 100 | 320 | 24.9/33.0/38.5 | 96 | 96.4 |
| Example 7 | MA | 85 | 50 | 100 | 320 | 25.8/34.5/36.7 | 95 | 97.0 |
| Example 8 | MA | 85 | 30 | 100 | 320 | 27.4/32.4/34.4 | 95 | 94.2 |
| Example 9 | MA | 85 | 20 | 100 | 320 | 27.5/33.8/34.0 | 86 | 95.3 |
| Example 10 | MA | 85 | 70 | 100 | 160 | 22.4/36.0/37.5 | 96 | 95.9 |
| Example 11 | MA | 85 | 70 | 100 | 640 | 25.6/33.8/37.8 | 96 | 97.2 |
| Example 12 | 1,4-BQ | 75 | 100 | 15 | 320 | 23.5/37.5/35.6 | 95 | 96.5 |
| Example 13 | 1,4-BQ | 85 | 30 | 100 | 320 | 27.5/32.5/34.6 | 95 | 94.6 |
| Example 14 | MAD | 75 | 100 | 15 | 320 | 23.5/37.7/35.6 | 94 | 96.8 |
| Example 15 | MAD | 85 | 30 | 100 | 320 | 27.3/32.5/34.3 | 96 | 94.1 |
| Example 16 | MN | 75 | 100 | 15 | 320 | 23.5/37.6/35.6 | 94 | 96.7 |
| Example 17 | MN | 85 | 30 | 100 | 320 | 27.4/32.5/34.6 | 95 | 94.5 |

[1] Molar equivalent with respect to Rh
[2] mol of DCPD added dropwise per minute with respect to 1 mmol of Rh
[3] GC area %
[4] Result of GC analysis after step 2

[Preparation of Polyester Resin]

Polyester resins were prepared using each of the TCDDM compositions of Comparative Examples and Examples by the following method.

In a 2000 mL four-neck flask equipped with a thermometer, a condenser, a mantle, a stirrer and a vacuum pump, 549.0 g of terephthalic acid and 6.3 g of trimellitic anhydride as an acid component, 117.9 g of 2-methyl-1,3-propanediol as an alcohol component and 521.5 g of TCDDM were placed, and tetrabutoxy titanium was added as an esterification catalyst.

When the temperature was slowly raised from room temperature to 240° C. and water or methanol as a by-product flowed out to a theoretical amount, tetrabutoxytitanium was added as a polycondensation catalyst, the temperature was raised to 260° C., and vacuum reaction was carried out for several hours. As a result, as shown in Table 1 below, copolymerized polyester resins having an intrinsic viscosity of 0.40 dL/g to 0.65 dL/g and a number average molecular weight of 17,000 g/mol to 19,000 g/mol were obtained.

Physical properties of the prepared polyester resins were measured by the following methods, and the results are shown in Table 2.

(1) Intrinsic Viscosity (IV)

0.36±0.0002 g of the sample was dissolved in 30 mL of ortho-chlorophenol at 150° C. for 15 minutes, and then the intrinsic viscosity of the sample was measured using a Ubbelohde viscometer in a thermostatic bath at 35° C.

(2) Glass Transition Temperature (Tg)

Using a differential scanning calorimeter (METTLER TOLEDO, DSC 1), about 6 mg to 10 mg of the polyester resin was filled in an aluminum pan, and the polyester resin was heated from room temperature to 280° C. at a rate of 10° C./min (first scan), and annealed at 280° C. for 3 min. Thereafter, the polyester resin was rapidly cooled to room temperature, and then heated again from room temperature to 280° C. at a rate of 10° C./min (second scan) to obtain a DSC curve.

When the polymer undergoes glass transition, the specific heat of the amorphous material increases, and the DSC curve shows a characteristic shift in the endothermic direction. Therefore, the temperature at which the maximum slope of the curve appeared at the point where the DSC curve showed a first step transition during heating was defined as the glass transition temperature (Tg) of the polyester resin.

(3) Number Average Molecular Weight (Mn) and Weight Average Molecular Weight (Mw)

The number average molecular weight and weight average molecular weight of each resin were measured using Tosoh's gel permeation chromatography (GPC) and RI detector.

0.03 g of the resin was dissolved in 3 mL of ortho-chlorophenol at 150° C. for 15 minutes, and then 9 mL of chloroform was added at room temperature to prepare a sample. The sample was injected at a temperature of 40° C. at a flow rate of 0.7 ml/min using 12 ml of ortho-chlorophenol:chloroform=1:3 (v/v) solution as an eluent for measurement. The values of Mw and Mn were derived using a calibration curve formed using polystyrene standards. 9 kinds of polystyrene standards having a molecular weight of 2,000/10,000/30,000/70,000/200,000/700,000/2,000,000/4,000,000/10,000,000 were used.

(4) Resin solubility 100 g of the sample was added to 500 ml of methyl ethyl ketone and stirred at 20° C. for 10 minutes. Thereafter, the solution was filtered to obtain an undissolved resin, which was dried in a vacuum oven, and then weighed. The weight of the undissolved resin was measured by the above method three times for each resin sample, and an average value was derived.

TABLE 2

| | Intrinsic viscosity (dl/g) | Glass transition temperature (° C.) | Mn (g/mol) | Mw (g/mol) | Resin solubility (g) |
|---|---|---|---|---|---|
| Comparative Example 1 | 0.49 | 104.1 | 17700 | 48000 | 78 |
| Comparative Example 2 | 0.49 | 104.2 | 17900 | 47700 | 71 |
| Comparative Example 3 | 0.50 | 103.9 | 18000 | 48200 | 82 |
| Comparative Example 4 | 0.49 | 104.4 | 17800 | 48100 | 76 |
| Comparative Example 5 | 0.51 | 103.7 | 17800 | 47700 | 75 |
| Comparative Example 6 | 0.49 | 104.0 | 18200 | 48200 | 79 |
| Example 1 | 0.51 | 104.5 | 17700 | 48000 | 28 |
| Example 2 | 0.50 | 104.3 | 17800 | 48000 | 21 |
| Example 3 | 0.52 | 102.4 | 17900 | 47800 | 3 |
| Example 4 | 0.51 | 103.2 | 17500 | 47200 | 24 |
| Example 5 | 0.51 | 104.1 | 17800 | 48100 | 17 |
| Example 6 | 0.50 | 102.4 | 18000 | 48200 | 15 |
| Example 7 | 0.49 | 103.3 | 17600 | 47700 | 27 |
| Example 8 | 0.49 | 103.3 | 17500 | 47100 | 21 |
| Example 9 | 0.51 | 104.2 | 17900 | 47300 | 11 |
| Example 10 | 0.50 | 101.2 | 17700 | 47900 | 14 |
| Example 11 | 0.51 | 102.3 | 17600 | 47200 | 12 |
| Example 12 | 0.51 | 104.3 | 17700 | 48000 | 16 |
| Example 13 | 0.49 | 103.8 | 17600 | 47800 | 22 |
| Example 14 | 0.50 | 103.7 | 17900 | 47900 | 18 |
| Example 15 | 0.50 | 103.2 | 17600 | 47500 | 20 |
| Example 16 | 0.51 | 103.5 | 17700 | 47900 | 17 |
| Example 17 | 0.49 | 103.6 | 17800 | 47800 | 21 |

Referring to Table 2, it was confirmed that the solubility of the polyester resins prepared using the TCDDM compositions of Examples 1 to 17 in the organic solvent was significantly superior to that of the polyester resins prepared using the TCDDM compositions of Comparative Examples 1 to 6.

What is claimed is:

1. A method of preparing a tricyclodecane dimethanol composition, the method comprising the steps of:
    performing a two-step hydroformylation reaction by:
        a) adding dropwise dicyclopentadiene at a temperature of 75° C. to 85° C. while maintaining a mixed gas of hydrogen and carbon monoxide at a pressure 20 bar to 150 bar in the presence of a catalyst composition including a rhodium-containing catalyst compound and 5 moles to 200 moles of an organophosphorus compound per 1 mole of rhodium, and a dienophile to form a reaction mixture; and
        b) after the dropwise addition of dicyclopentadiene is finished, further reacting the reaction mixture while heating the reaction mixture to 130° C. and maintaining the pressure of the CO/H$_2$ mixed gas;
    wherein the method further comprises the steps of:
    performing a hydrogenation reaction of tricyclodecane dialdehyde obtained by the two-step hydroformylation reaction in the presence of a hydrogenation catalyst,
    wherein the tricyclodecane dimethanol composition includes 20 parts by weight to 35 parts by weight of a first structural isomer represented by the following Formula 1-1, 27 parts by weight to 42 parts by weight of a second structural isomer represented by the following Formula 1-2, and 27 parts by weight to 42 parts by weight of a third structural isomer represented by the following Formula 1-3, based on 100 parts by weight of the composition:

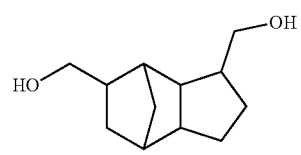

[Formula 1-1]

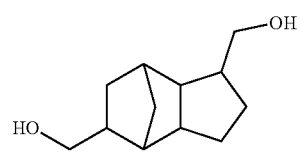

[Formula 1-2]

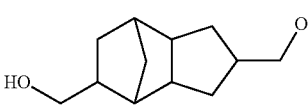

[Formula 1-3]

2. The method of claim 1, wherein the organophosphorus compound is included in an amount of 10 moles to 100 moles per 1 mole of rhodium.

3. The method of claim 1, wherein in a step of the two-step hydroformylation reaction, the dropwise addition of dicyclopentadiene is performed such that the number of moles of dicyclopentadiene added per minute with respect to 1 mmol of the rhodium element in the catalyst composition is 10 mmol to 10,000 mmol.

4. The method of claim 1, wherein the dienophile is one or more selected from the group consisting of maleic anhydride, tetracyanoethylene, maleic acid, maleonitrile, 2-methylenemalononitrile, dialkyl 2-methylenemalonate, 2-methylenemalonic acid, 2-methylenemalonaldehyde, 3-methylenepentane-2,4-dione, fumaraldehyde, ethene-1,1,2,2-tetracarbaldehyde, 1,4-benzoquinone, and dialkyl maleate.

5. The method of claim 1, wherein the dienophile is used in an amount of 0.001 part by weight to 1.0 part by weight, based on 100 parts by weight of the dicyclopentadiene.

6. The method of claim 1, wherein the hydrogenation catalyst is a Ru/C catalyst.

7. The method of claim 1, wherein the hydrogenation reaction is performed at a temperature of 80° C. to 250° C. and a pressure of 20 bar to 200 bar.

* * * * *